United States Patent [19]

Murakami et al.

[11] 4,355,014
[45] Oct. 19, 1982

[54] STABLE CALCIUM HYPOCHLORITE COMPOSITION AND METHOD FOR MANUFACTURE THEREOF

[75] Inventors: Tsugio Murakami; Kazushige Igawa; Yoichi Hiraga, all of Shin-nanyo, Japan

[73] Assignee: Toyo Soda Manufacturing Co., Ltd., Shin-nanyo, Japan

[21] Appl. No.: 152,720

[22] Filed: May 23, 1980

[30] Foreign Application Priority Data

May 29, 1979 [JP] Japan ................................ 54-65554
Jul. 17, 1979 [JP] Japan ................................ 54-89777

[51] Int. Cl.$^3$ ........................ C01F 11/24; C01B 11/06; C09K 3/00
[52] U.S. Cl. ............................. 423/265; 252/186.37; 252/186.21; 423/474
[58] Field of Search .................. 252/187 H; 423/155, 423/265

[56] References Cited

U.S. PATENT DOCUMENTS 3,669,894  6/1972  Faust ................................ 252/187 H
3,793,216  2/1974  Dychdala et al. ............... 252/187 H
3,953,354  4/1976  Faust ................................ 252/187 H

FOREIGN PATENT DOCUMENTS 52-111497  9/1977  Japan ............................ 252/187 H

OTHER PUBLICATIONS

Hackh's Chemical Dictionary, Grant, Blakiston Company, Philadelphia, pp. 157, 158, 492, (1970).

Primary Examiner—John M. Ford
Assistant Examiner—Robert C. Whittenbaugh
Attorney, Agent, or Firm—Armstrong, Nikaido, Marmelstein & Kubovcik

[57] ABSTRACT

A stable calcium hypochlorite composition and a method for the preparation thereof. The composition has a calcium hypochlorite anhydride and/or a calcium hypochlorite dihydrate used as main constituent and comprises at least 60 wt % of calcium hypochlorite; at least 5 wt % of calcium hydroxide; at least 4 wt % of water content; and 5 wt % or less of than that calcium chloride. The composition is stable and decomposes only in a less degree at a high temperature and during storage over a long period.

11 Claims, No Drawings

STABLE CALCIUM HYPOCHLORITE COMPOSITION AND METHOD FOR MANUFACTURE THEREOF

BACKGROUND OF THE INVENTION

1. Field of the Invention

This invention relates to a stable calcium hypochlorite composition which decomposes little even when left in storage over a long period and at a high temperature and also relates to a method for the preparation of the composition.

2. Description of the Prior Art

Calcium hypochlorite is a strong oxidizing agent and is an important compound being widely in use for treatment of water of swimming pools, water supplies and swerages and also for bleaching cotton and pulp on account of the excellent sterilizing and bleaching effects obtainable therefrom.

A composition which is generally known by the name of "high test hypochlorite" and is commercially available is composed of calcium hypochlorite as its main constituent having 60 wt %, 65 wt % or 70 wt % of available chlorine content.

The calcium hypochlorite composition is mostly used for sterilization of the water of swimming pools and the season during which it is used for that purpose is summertime. Accordingly, the temperature at which it is transported or stored sometimes exceeds 40° C. Therefore, it is generally desired to obtain a stable calcium hypochlorite composition in which the calcium hypochlorite decomposes little at a high temperature.

To meet this requirement, there is available a calcium hypochlorite composition which is virtually anhydrous. However, this anhydrous calcium hypochlorite composition tends to suddenly decompose when it is brought into contact with flames, sparks and organic matters. In other words, it tends to explode and requires much caution in handling it. Further, it cannot be easily handled because it produces much dust. Another disadvantage lies in that it necessitates the use of much energy for dehydration of it during the manufacture thereof. These disadvantages can be eliminated by allowing it to keep a high water content therein. However, it is well known that the stability of the calcium hypochlorite decreases as the water content increases in the calcium hypochlorite composition.

To solve this problem, many attempts have been made to obtain a stable calcium hypochlorite composition having a high water content.

For example, a U.S. Pat. No. 3,793,216 (corresponding to a Japanese patent application laid open No. 48-65183) has proposed a calcium hypochlorite composition which is prepared by adding a water soluble inorganic hydrate to a calcium hypochlorite to make a water content thereof 3 to 13 wt %. Further, a Japanese patent application laid open No. 51-111497 has proposed a calcium hypochlorite composition which is prepared by mixing a calcium hypochlorite having 16 to 22 wt % of water content with a virtually anhydrous calcium hypochlorite having its water content not exceeding 2 wt % and which is arranged to have at least 50 wt % of available chlorine included therein.

However, the methods employed by these prior arts are not only uneconomical because they require the addition of an expensive water-soluble inorganic hydrate or the use of two kinds of calcium hypochlorite composite of different compositions, but also, they do not give stable products according to the results of the studies conducted by the present inventors. They examined the effects of the water content and temperature on the stability of a calcium hypochlorite composition to find that, with the decomposition of calcium hypochlorite which takes place in a composite having 2 to 3 wt % of water content at a temperature of 20° C. used as reference, the degree of its decomposition increases by about four times at 40° C. In case where the water content is arranged to be 5 to 6 wt %, the decomposition increases by 7 to 8 times at 40° C. When the water content exceed 7 wt % at 40° C., the decomposition increases at least by 10 times and the composition completely loses its value as commercial product.

The inventors further conducted their study based on this finding in an effort to find a calcium hypochlorite composition which remains stable even at a high water content and at a high temperature. As a result of this study, they have found that a calcium hypochlorite composition having a high calcium hypochlorite content can be greatly stabilized when it contains at least 5 wt % of calcium hydroxide and 5 wt % or less than that of calcium chloride and when it has at least 4 wt % of water content and thus came to complete the present invention.

SUMMARY OF THE INVENTION

It is therefore a general object of the invention to provide a stable calcium hypochlorite composition which has a calcium hypochlorite anhydride and/or a calcium hypochlorite dihydrate as main constituent and is composed of at least 60 wt % of calcium hypochlorite, at least 5 wt % of calcium hydroxide, at least 4 wt % of water content and 5 wt % or less than that of calcium chloride.

The above stated composition is extremely stable and has its calcium hypochlorite decompose only to a very slight degree even at a high temperature exceeding 40° C. Furthermore, the composition can be economically prepared because it does not require the use of any special chemicals for the preparation thereof.

The calcium hydroxide to be used in accordance with the present invention may be selected out of the group consisting of free calcium hydroxide and calcium hydroxides constituting semibasic calcium hypochlorite, dibasic calcium hypochlorite, calcium oxychloride, etc. ($CaCl_2.3Ca(OH).12H_2O$, $CaCl_2.Ca(OH)_2.H_2O$, etc.). However, it is preferable to use free calcium hydroxide. They are readily recognizable by the diffraction of X-rays.

The stabilizing effect of the calcium hydroxide varies with the quantities of the calcium hypochlorite content, the water content and the calcium chloride content. The stabilizing effect of the calcium hydroxide greatly increases when the quantity of the calcium hypochlorite content exceeds 60 wt % but is not much when it is less than 60 wt %. On the other hand, the calcium hydroxide produces no effect on a virtually anhydrous calcium hypochlorite composite having less than 2 wt % of water content because, as mentioned in the foregoing, such a composition is very stable to begin with.

However, this condition suddenly changes when the water content comes to exceed 4 wt % and there emerges a stabilizing effect of the calcium hydroxide. Then, the stabilizing effect is particularly salient at a high temperature exceeding 40° C. This stabilizing effect becomes conspicuous in case where the calcium hydroxide content exceeds 5 wt %. Particularly, the stabilizing effect is enhanced when the calcium hydroxide is free calcium hydroxide. Further, although the stabilizing effect increases according as the quantity of the calcium hydroxide content increases, the stabilizing effect comes to increase in a less degree when the calcium hydroxide content exceeds 10 wt %. Besides, in such a case, the dust is produced to an excessive extent and the solution velocity comes to decrease. Therefore, it is not desirable to have the calcium hydroxide content exceed 10 wt %.

In view of this, the calcium hydroxide content is set between 5 and 10 wt % and preferably between 6 and 8 wt %. Although it is difficult to completely explain the stabilizing effect of the calcium hydroxide, it is presumed to be as follows:

Chlorine gas is discharged as the calcium hypochlorite decomposes. Chlorine gas discharging reactions include a reaction which can be expressed by Formula (1) as shown below:

$$Ca(ClO)_2 + CaCl_2 + 2H_2O \rightarrow 2Ca(OH)_2 + 2Cl_2 \ldots (1)$$

Then, the chlorine gas which is produced in this manner comes to further accelerate the decomposition of the calcium hypochlorite by a reaction which can be expressed by Formula (2) as shown below:

$$3Ca(ClO)_2 \xrightarrow{[Cl_2]} Ca(ClO_3)_2 + 2CaCl_2 \ldots (2)$$

In other words, in the calcium hypochlorite decomposing reaction, the chlorine gas is performing a catalytic action. In case where there is calcium hydroxide, the chlorine gas produced by the decomposition is reacted and absorbed by the calcium hydroxide. It is, therefore, believed that this prevents the reactions expressed by Formulas (1) and (2) from proceeding to stabilize the calcium hypochlorite. Further, the reason why free calcium hydroxide has a greater effect seems to be that the free calcium hydroxide is capable of absorbing the chlorine gas at a higher speed and has a greater absorbing capacity.

It is another essential condition for the composition of the present invention to have at least 4 wt % of water content. The stability of the composite remains almost unchanged with the water content between 4 wt % and 22 wt %. However, the dust is produced in a less degree when the water content exceeds 7 wt %, so that the composition can be handled without difficulty. Besides, such a degree of water content is preferable also because it does not require much drying energy during the preparation of the composition. On the other hand, the stabilizing effect somewhat decreases when the water content exceeds 22 wt %.

Though it is nothing else but a mere presumption, water content above 22 wt % is considered free water because 22 wt % of water content coincides with the crystal water content in the dihydrate of calcium hypochlorite and the presence of this free water seems to hinder the stabilization. Accordingly, in accordance with this invention, the preferred water content of the composition is in the range of 7~22 wt %.

It is a further essential condition for the calcium hypochlorite composition of the invention to have 5 wt % or less than that of calcium chloride content therein. The stability of the composite lowers when the calcium chloride content exceeds 5 wt %.

While the calcium hypochlorite composition of the invention must have the calcium hypochlorite content, the calcium hydroxide content, the water content and the calcium chloride content restricted within their prescribed ranges respectively, there is no particular restriction for other constituents. As for the constituents other than the above stated four constituents, the presence of sodium chloride is preferable.

It is preferable that the calcium hypochlorite composition is a virtually homogeneous state. The "homogeneous state" as used herein means a condition in which the minimal units, i.e. the crystals, of the constituents of the composition are uniformly mixed. For example, a sufficient stabilizing effect cannot be expected with the calcium hypochlorite covered by the calcium hydroxide or, conversely, with the latter covered by the former. Therefore, in preparing the calcium hypochlorite composition into a granulated product, it is preferable to homogeneously mix the crystals of the constituents before granulating the composition into the granulated product.

There is no particular prescription for the particle diameter of the invented composition of calcium hypochlorite. However, the composition is preferably granulated to have a grain size between 8 and 200 meshes (as defined by JIS Z8801, which applies hereinafter).

It is an advantageous feature of the calcium hypochlorite composition of the invention that, compared with the conventional products, the stability which is a very important property is saliently improved at a high temperature exceeding 40° C. Further features of the composition include:

(1) Despite of the relatively high calcium hydroxide content, the composition produces little dust and, therefore, is easy to handle.

(2) The solution velocity of the composition can be controlled by adjusting the water content and the calcium hydroxide content thereof. The solution velocity can be increased by increasing the water content and by decreasing the calcium hydroxide content. Conversely, an arrangement reverse to that results in a lowered solution velocity.

(3) The composition does not require the use of any special chemicals.

(4) Since the composition is prescribed to have a high water content, it can be prepared with a less degree of drying energy consumption.

These are advantages which cannot be expected from the conventional calcium hypochlorite composition. In addition to these advantages, it is amazing that, unlike the conventional compositions, the invented calcium hypochlorite composition has a great stability against acid. This is an unexpected advantage of the invented composite.

The stable calcium hypochlorite composition can be prepared by methods which mainly include the following:

(a) A wet cake is obtained by filtrating a slurry of a calcium hypochlorite dihydrate. Calcium hydroxide is added to the wet cake. With the calcium hydroxide added, the wet cake is mixed therewith and dried.

(b) After the wet cake obtained by the method (a) is dried, the calcium hydroxide is added to and mixed with the dried cake. After the addition and mixing process, a further drying process may be carried out.

(c) Calcium hydroxide is added to a slurry of a calcium hypochlorite and is mixed therewith. The mixture is filtrated. Then, a wet cake thus obtained is dried.

(d) In preparing a calcium hypochlorite dihydrate by chlorinating a calcium hydroxide, the calcium hydroxide which has not reacted is left over. Then, the slurry thus obtained is filtrated to obtain a wet cake. The wet cake is dried.

Of these method, the methods (a) and (b) are preferable because they can be carried out without difficulty and permit easy adjustment of each of the constituents. In other words, for the preparation of the stable calcium hypochlorite composition of the invention, it is most preferable to have a calcium hydroxide added to and mixed with a raw calcium hypochlorite composition which is mainly composed of a calcium hypochlorite anhydride and/or a calcium hypochlorite dihydrate and to make the composition comprise at least 60 wt % of calcium hypochlorite, at least 5 wt % of calcium hydroxide, at least 4 wt % of water content and 5 wt % of less than that of calcium chloride.

This raw calcium hypochlorite composition has the calcium hypochlorite anhydride and/or the calcium hypochlorite dihydrate as the main constituent thereof and does not have a semi-basic calcium hypochlorite or a dibasic calcium hypochlorite as its main constituent. The raw composition is not granulated nor tableted into a shape.

Further, raw basic calcium hypochlorite composition preferably comprises in the ratio of 70 parts by weight or less than that of water content and 8 parts by weight or less of calcium chloride to 100 of the calcium hypochlorite. In this case, the addition and mixing of the calcium hydroxide can be very easily carried out and the stability of the calcium hypochlorite composition obtained from the use of this raw composition increases to a great extent. Further, the raw calcium hypochlorite composition preferably has a water content in such a degree that the calcium hypochlorite of the raw composition virtually corresponds to the dihydrate of calcium hypochlorite.

The calcium hydroxide to be added may be selected out of the group consisting of free calcium hydroxide, semi-basic calcium hypochlorite, dibasic calcium hypochlorite, calcium oxychloride and calcium oxide. The "free calcium hydroxide" is a material such as lime hydrate, which exists in an isolated or independent form and not in the form of a double salt. However, for the purpose of stabilization, it is preferable to use a powder of free calcium hydroxide (hereinafter will be called a calcium hydroxide powder). The calcium hydroxide powder in usable for universal purposes and is also in use as material for the preparation of calcium hypochlorite. It is therefore economical to use the calcium hydroxide powder. The particle diameter of the calcium hydroxide powder is preferably as small as possible. The usable calcium hydroxide powder passes through a 100 mesh screen and preferably passes through a 200 mesh screen. Further, it is preferable that the calcium hydroxide powder contains virtually no free water. The presence of free water not only produces a double salt of the calcium hydroxide but also makes the powder viscous to make mixing difficult. Therefore, with free water included, it becomes difficult to obtain a homogeneous composition. The term "water content which virtually contains no free water" as used here means less than 10 wt % of water content. The use of a wet cake of calcium hydroxide or the milk of lime is not suitable. Further, a sufficient stabilizing effect cannot be attained when the calcium hydroxide powder is in a state of being covered with calcium carbonate. For example, a sufficient effect cannot be expected from the use of the calcium hydroxide powder that has been left intact in the atmosphere over a long period. To give a criterion by way of example, the calcium hydroxide powder contains less than 10 wt % and preferably less than 5 wt % of calcium carbonate.

Although the stability of the calcium hypochlorite composition can be increased even when there is a high calcium hydroxide content in the raw calcium hypochlorite composition, the increase in the stability is only to a minor degree. On the other hand, the stability varies to a great extent with the addition quantity of calcium hydroxide. In other words, the stabilizing effect saliently increases when the quantity of the calcium hydroxide to be added is at least 2 parts by weight to 100 of the raw calcium hypochlorite composite as reduced to $Ca(OH)_2$ (hereinafter this will apply to the calcium hydroxide to be added). The stabilizing effect is greatly enhanced when the addition quantity of the calcium hydroxide is at least 5 parts by weight. However, the addition quantity of the calcium hydroxide in excess of 10 parts by weight not only dulls the rate of the increase of the stabilizing effect but also causes the dust to be produced in an increased degree and slows down the solution velocity. Therefore, it is preferable to have the calcium hydroxide added in quantity between 5 and 10 parts by weight. When a free calcium hydroxide powder is employed as the calcium hydroxide, the stabilizing effect can be further increased.

As previously disclosed by the present applicant in Japanese patent applications laid open No. 53-35357 and 54-127897, it is preferable to use a raw calcium hypochlorite composition mainly consisting of a coarse calcium hypochlorite dihydrate or its dried product which is obtained by adding as seed crystals a prismatic calcium hypochlorite dihydrate having the axes a and b (in the direction of width) and axis c (in the direction of thickness) in the ratio of:

$$0.5 \leq b/a \leq 2.0$$
$$c/a \geq 1.5$$

and having the axis c measure at least 5 microns during the crystallization process of the calcium hypochlorite dihydrate. With this raw composite employed, the stability of a calcium hypochlorite composition still further increases. Besides, the use of this raw composition greatly facilitates the process of mixing the calcium hydroxide. Further, it is desirable that sodium chloride be a constituent of the raw calcium hypochlorite composition, however the calcium hypochlorite, calcium hydroxide, water and calcium chloride are also employed as constituents of the raw composition.

In accordance with the present invention, mixing is carried out for the purpose of obtaining a virtually homogeneous composition and may be carried out with any of a ribbon mixer, a V-cone mixer, a screw mixer or the like that is normally used for mixing powders. In case where mixing is to be carried out with a gas such as air, the use of a cyclone or a bag filter or the like in combination with the mixer might be necessary to prevent the powder from spattering. The term "a virtually homogeneous composition" as used herein means a state in which the minimal units of constituents of the composition, i.e. the crystals of the constituents, are uniformly mixed and distributed. For example, the stabilizing effect decreases when the calcium hypochlorite is covered by the calcium hydroxide or conversely, the latter is covered by the former.

Further, in obtaining the composition of the present invention, the composition prepared by adding and mixing the calcium hydroxide to and with the raw calcium hypochlorite composition may be dried, granulated and shaped as necessary. The drying, granulating and shaping processes are carried out in cases where it is desirous to change the water content, the calcium hypochlorite content and the shape of the calcium hypochlorite composition and are not required where such changes are not necessary.

The drying process is carried out for adjustment of the water content. When the water content is too high, it should be lowered by drying. Conversely, when the water content should be increased, either water may be added or a calcium hypochlorite composite having a high water content may be mixed.

The granulating process is carried out for adjusting the particle diameter or for making it larger. A preferred particle diameter range is normally from 8 to 200 meshes. With the particle size adjusted to be within this range, the composition can be handled without difficulty and can be prevented from raising a dust. Where two processes of drying and granulating are to be carried out, the granulation may be either carried out after drying or before drying. In the latter case, although the drying process is not easy, the composition is granulated in a state of having a high water content to facilitate the granulating process and can be strongly granulated. Besides, the dust can be prevented from being produced and the calcium hydroxide can be prevented from spattering during the drying process. Therefore, the latter is preferable.

The shaping process is carried out for the purpose of obtaining tablets. In this case, the shaping process may be either carried out after the calcium hydroxide is added and mixed or after the granulating process. It is also possible to carry out the drying process in combination with these two processes. It is preferable, however, to carry out tthe shaping process after the granulating process as generally practiced or with the drying process carried out between the granulating and shaping processes.

Further, sodium chloride and calcium hypochlorite may be added in such a way as to have at least 60 wt % of calcium hypochlorite, at least 5 wt % of calcium hydroxide, at least 4 wt % of water content and 5 wt % of less than that of calcium chloride.

The above and further objects, features and advantages of the invention will become apparent from the following description of embodiment and comparison examples wherein: Unless otherwise stated the parts and percentage of the constituents employed are by weight; and the term "decomposition rate of calcium hypochlorite" as used in these examples means:

$$\left(1 - \frac{Ca(ClO)_2 \text{ after test storage (wt \%)}}{Ca(ClO)_2 \text{ before test storage (wt \%)}}\right) \times 100$$

DETAILED DESCRIPTION OF PREFERRED EMBODIMENTS

Embodiment Example 1

First 9.5 parts of a calcium hydroxide powder of 97.0% purity was added to 251 parts of a wet cake of a calcium hypochlorite dihydrate comprising 59.0% of calcium hypochlorite, 1.2% of calcium hydroxide, 29.5% of water content and 7.5% of sodium chloride with mixing carried out by means of a ribbon mixer.

Next, a drying process was carried out with a hot air dryer, which was kept at 90° C., to obtain 200 parts of a homogeneous calcium hypochlorite composition comprising 73.2% of calcium hypochlorite, 6.0% of calcium hydroxide, 7.2% of water content, 9.3% of sodium chloride and 2.0% of calcium chloride. It was confirmed by diffraction of X-rays that almost the whole of the calcium hydroxide in the composite thus obtained was free calcium hydroxide.

Then, 50 g of the composition was put in a 100 ml polyethylene container and kept there at 40° C. for 50 days in one test and at 65° C. for 2 days in another test. The decomposition rates of the calcium hypochlorite of the composition obtained by these tests were 9.0% and 11.2% respectively.

Meanwhile, an experiment for comparison was conducted in the same manner as described in the foregoing with the exception of the same addition quantity of a sodium chloride powder of 99% purity was added in place of the calcium hydroxide powder to obtain a homogeneous calcium hypochlorite composition comprising 72.5% of calcium hypochlorite, 1.8% of calcium hydroxide, 7.0% of water content, 14.3% of sodium chloride and 2.2% of calcium chloride. The composition thus obtained for comparison was also subjected to the same tests as described in the foregoing. Then, the decomposition rates of calcium hypochlorite was 20.5% in the test carried out at 40° C. for 50 days and 20.2% in the test carried out at 65° C. for 2 days.

Embodiment Example 2

A calcium hypochlorite composition (hereinafter will be called the dry product) was obtained by drying a wet cake of a calcium hypochlorite dihydrate. The dry product thus obtained comprised 76.8% of calcium hypochlorite, 1.7% of calcium hydroxide, 10.9% of water content, 2.8% of calcium chloride and 5.0% of sodium chloride. To 95 parts of this dry product was added 5 parts of a calcium hydroxide powder of 97% purity with mixing carried out using a ribbon mixer to obtain a calcium hypochlorite composition comprising 73.0% of calcium hypochlorite, 6.6% of calcium hydroxide, 10.2% of water content, 2.6% of calcium chloride, and 4.8% of sodium chloride. The composition thus obtained was subjected to the same tests as in Embodiment Example 1 to find that: The decomposition rate of calcium hypochlorite was 8.5% in the test carried out at 40° C. for 50 days and 14.1% in the test carried out at 65° C. for 2 days.

Another composition was prepared in the same manner as described in the foregoing with the exception of that the calcium hydroxide powder was replaced in this case with the same addition quantity of a sodium chloride powder of 99% purity. The composition thus obtained was subjected to the same tests to find that the decomposition rate of calcium hypochlorite was 26.5% at 40° C. over the period of 50 days and 32.8% at 65° C. over the period of 2 days.

Embodiment Example 3

To 72.3 parts of the dry product obtained in Embodiment Example 2 was added 27.7 parts of a commercially available 60% high test hypochlorite powder which had a semi-basic calcium hypochlorite used as main constituent and which comprised 64.7% of the calcium hypochlorite, 21.9% of calcium hydroxide, 2.6% of water content and 7.1% of calcium chloride. They were mixed by means of a ribbon mixer to obtain a calcium hypochlorite composition comprising 73.3% of calcium hypochlorite, 7.4% of calcium hydroxide, 8.6% of water content, 4.0% of calcium chloride and 3.6% of sodium chloride.

This composition was subjected to the same tests as in Embodiment Example 1. The decomposition rate of calcium hypochlorite was 16.2% at 40° C. over the period of 50 days and 20.2% at 65° C. over the period of 2 days.

Embodiment Examples 4–8 and Comparison Examples 1–3

The decomposition rates of calcium hypochlorite contained in calcium hypochlorite compositions of different compositions were examined by subjecting these composites to the same tests as in Embodiment Example 1 by carrying out the tests at 40° C. for 50 days and at 65° C. for two days.

Further, it was confirmed through diffraction of X-rays that the calcium hydroxide used was virtually free calcium hydroxide.

|  | Compositions | | | | | Decomposition rates | |
| --- | --- | --- | --- | --- | --- | --- | --- |
|  | Ca(ClO)$_2$ % | Ca(OH)$_2$ % | H$_2$O % | CaCl$_2$ % | NaCl % | 40° C. for 50 days, % | 65° C. for two days, % |
| Embodiment Example 4: | 63.0 | 5.3 | 5.7 | 4.2 | 18.8 | 8.3 | 10.8 |
| Embodiment Example 5: | 67.3 | 8.2 | 7.6 | 3.2 | 11.1 | 8.6 | 11.9 |
| Embodiment Example 6: | 72.0 | 10.5 | 13.4 | 2.1 | 0.0 | 8.5 | 15.6 |
| Embodiment Example 7: | 77.5 | 5.6 | 11.6 | 3.4 | 0.0 | 9.7 | 17.1 |
| Embodiment Example 8: | 83.2 | 6.1 | 7.2 | 1.8 | 0.0 | 10.0 | 9.9 |
| Comparison Example 1: | 70.4 | 3.5 | 17.7 | 2.7 | 4.1 | 42.0 | 54.7 |
| Comparison Example 2: | 74.3 | 2.2 | 10.1 | 2.2 | 8.7 | 31.5 | 30.8 |
| Comparison Example 3: | 73.5 | 6.5 | 10.6 | 7.2 | 0.0 | 25.0 | 28.6 |

Embodiment Example 9

A wet cake of a calcium hypochlorite dihydrate was prepared with a great amount of non-reacted calcium hydroxide left therein. The wet cake comprised 43.5% of calcium hypochlorite, 4.2% of calcium hydroxide, 43.5% of water content, 0.5% of calcium chloride and 6.8% of sodium chloride.

Then, the wet cake was dryed by means of a hot air dryer which was kept at 90° C. to obtain a calcium hypochlorite composition comprising 68.2% of calcium hypochlorite, 6.9% of calcium hydroxide, 7.0% of water content, 2.3% of calcium chloride and 11.0% of sodium chloride. The composition thus obtained was subjected to tests which were conducted in the same manner as in Embodiment Example 1 to find that the decomposition rate of the calcium hypochlorite in this composition was 14.0% at 40° C. over the period of 50 days and 18.0% at 65° C. over the period of two days.

Embodiment Example 10

A wet cake of a calcium hypochlorite dihydrate was prepared to be comprising 46.5% of calcium hypochlorite, 1.4% of calcium hydroxide, 41.9% of water content, 0.5% of calcium chloride and 7.5% of sodium chloride. To 100 parts of this wet cake was added 3.0 parts of a calcium hydroxide powder which was of 97% purity and of particle size passing through a 200 mesh screen with mixing carried out by means of a ribbon mixer.

Then, the composition was dried with a hot air dryer which was kept at 90° C. to obtain a calcium hypochlorite composition comprising 67.1% of calcium hypochlorite, 6.0% of calcium hydroxide, 7.1% of water content, 2.7% of calcium chloride and 11.5% of sodium chloride. The composition thus obtained was subjected to tests which were carried out in the same manner as in Embodiment Example 1. The decomposition rate of the calcium hypochlorite of the composition was 13.5% at 40° C. over the period of 50 days and 17.5% at 65° C. over the period of two days.

EMBODIMENT EXAMPLE 11

A raw calcium hypochlorite composition was prepared by drying a wet cake of a calcium hypochlorite dihydrate to be comprising 63.0% of calcium hypochlorite, 2.1% of calcium hydroxide, 17.5% of water content, 1.5% of calcium chloride and 13.1% of sodium chloride. To 95.2 parts of this raw composite was added 4.8 parts of a calcium hydroxide powder which was of 97% purity and of particle size passing through a 200 mesh screen with mixing carried out by means of a ribbon mixer. The mixture processed into a thin plate shape with a rolling mill. Then, this plate shaped mixture was cracked into a granulated state and dried with a hot air dryer which was kept at 90° C. to obtain a calcium hypochlorite composition comprising 68.0% of calcium hypochlorite, 7.9% of calcium hydroxide, 4.5% of water content, 1.8% of calcium chloride and 14.5% of sodium chloride. The composition thus obtained was then subjected to tests which were carried out in the same manner as in Embodiment Example 1. The decomposition rate of the calcium hypochlorite of the composition was 6.0% at 40° C. over the period of 50 days and 6.9% at 65° C. over the period of two days.

EMBODIMENTS EXAMPLES 12–14 AND COMPARISON EXAMPLE 4

A raw calcium hypochlorite composition was prepared by drying a wet cake of a calcium hypochlorite dihydrate to be comprising 75.0% of calcium hypochlorite, 2.6% of calcium hydroxide, 8.0% of water content, 1.0% of calcium chloride and 9.4% of sodium chloride. To this raw composition was added a calcium hydroxide powder which was of 97% purity and of particle size passing through a 200 mesh screen. Further a sodium chloride of 99% purity was added to the raw composition. Mixing was carried out with a ribbon mixer to obtain a calcium hypochlorite composition for the purpose of adjusting the calcium hypochlorite content and the water content. The composition thus obtained was subjected to tests which were carried out in the same manner as in Embodiment Example 1 to find the decomposition rate of the calcium hypochlorite of the composition.

The addition quantity of each additive used and the decomposition rate of the calcium hypochlorite of the composition obtained in each of the embodiment examples and the comparison example as described in the foregoing were as shown in the following table:

| | Blending ratio, part (see Notes) | | | Calcium hypochlorite compositions | | | | | Decomposition rates, % | |
|---|---|---|---|---|---|---|---|---|---|---|
| | A | B | C | Ca(ClO)$_2$ % | Ca(OH)$_2$ % | H$_2$O % | CaCl$_2$ % | NaCl % | 40° C. 50 days | 65° C. 2 days |
| Embodiment Example 12: | 90 | 3 | 7 | 67.4 | 5.3 | 7.5 | 0.9 | 15.5 | 8.7 | 12.9 |
| Embodiment Example 13: | 90 | 5 | 5 | 67.5 | 7.2 | 7.3 | 0.9 | 13.3 | 8.0 | 11.0 |
| Embodiment Example 14: | 90 | 10 | None | 67.5 | 12.2 | 7.3 | 0.9 | 8.5 | 7.8 | 10.5 |
| Comparison Example 4: | 90 | None | 10 | 67.4 | 2.2 | 7.4 | 0.9 | 18.8 | 22.0 | 23.9 |

Notes
A: A basic calcium hypochlorite composite
B: A calcium hydroxide powder (passing through a 200 mesh screen) of 97% purity
C: A sodium chloride powder of 99% purity

EMBODIMENT EXAMPLE 15

Using the raw calcium hypochlorite composition of Embodiment Example 12, 10 parts of a dibasic calcium hypochlorite powder comprising 44.2% of calcium hypochlorite, 47.5% of calcium hydroxide, 2.3% of water content and 3.4% of calcium chloride and 5 parts of a sodium chloride powder of 99% purity were added to 85 parts of the raw calcium hypochlorite composition. Mixing was carried out with a ribbon mixer to obtain a calcium hypochlorite composition comprising 68.0% of calcium hypochlorite, 7.0% of calcium hydroxide, 7.0% of water content, 1.3% of calcium chloride and 13.0% of sodium chloride.

The composition thus obtained was subjected to tests which were carried out in the same manner as in Embodiment Example 1. The decomposition rate of calcium hypochlorite was 14.0% at 40° C. over the period of 50 days and 17.3% at 65° C. over the period of two days.

Comparison Example 5

A basic calcium hypochlorite composition was prepared by drying a wet cake of a calcium hypochlorite dihydrate. The raw composition comprised 70.3% of calcium hypochlorite, 2.2% of calcium hydroxide, 7.5% of water content, 8.2% of calcium chloride and 9.5% of sodium chloride. To 95 parts of this raw composition was added 5 parts of a calcium hydroxide powder of 97% purity passing through a 200 mesh screen in particle size. Mixing was carried out with a ribbon mixer to obtain a calcium hypochlorite composition comprising 66.5% of calcium hypochlorite, 7.0% of calcium hydroxide, 7.0% of water content, 7.9% of calcium chloride and 9.0% of sodium chloride. The composition thus obtained was subjected to tests which were carried out in the same manner as in Embodiment Example 1. The decomposition rate of calcium hypochlorite was 20.3% at 40° C. over the period of 50 days and 22.5% at 65° C. over the period of two days.

EMBODIMENT EXAMPLE 16

Using a 1 liter crystallization tank equipped with a stirrer, 30 g of a 10% aqueous solution of citric acid, 112 g of calcium hydroxide, 239 g of a 48% aqueous solution of caustic soda and 449 g of water were put in the crystallization tank. While keeping the crystallization tank at 15° C., 201 g of chlorine gas was blown into the tank at a rate of about 150 g/hr-l. The pH value was 10.3 when chlorination was completed. Through this process, a prismatic calcium hypochlorite dihydrate, i.e. a slurry of prismatic seed crystals, having a shape close to a cylindrical shape was obtained. The seed crystal measured 5-15 microns in axes a and b and 20-120 in axis c with c/a being about 7. The slurry concentration was 9.5%.

Following this, a 1 liter cylindrical crystallization tank equipped with an overflow pipe was arranged to have an aqueous solution containing 4.0% of Ca(ClO)$_2$ and 36.0% of CaCl$_2$ introduced thereinto at a rate of 76.9 g/hr, 40% Ca(OH)$_2$ slurry at a rate of 88.6 g/hr, chlorine gas at a rate of 33.1 g/hr and the above stated prismatic seed crystal slurry at a rate of 8.42 g/hr. A chlorinating process was carried out with this crystallization tank kept at 30° C. while the above stated matters were separately and continuously introduced into the tank. Concurrently with this chlorination process, a slurry was taken out at a rate of 207 g/hr. The prismatic seed crystals grew well. An apparent crystal sojourning time was 5 hours. After a period of 45 hours, there was produced a slurry of a coarse calcium hypochlorite dihydrate which had a shape close to a square top double pyramidal shape measuring 20 to 400 microns in axes a and b and 20 to 150 microns in axis c thereof.

The slurry of this coarse calcium hypochlorite dihydrate was subjected to a separating process which was carried out for one minute with a basket centrifuge at 3000 rpm. The product thus obtained was washed with water for two minutes to obtain a washed cake comprising 68.5% of calcium hypochlorite, 0.8% of calcium hydroxide, 28.4% of water content and 0.8% of calcium chloride. The quantity of the water used for washing was about 65% of the washed cake.

To 100 parts of this washed cake were added 5 parts of a calcium hydroxide powder of 97% purity, passing through a 200 mesh screen in particle size, and 5 parts of a sodium chloride powder of 99% purity. Mixing was carried out with a ribbon mixer. The mixture was dried with a hot air dryer which was kept at 90° C. to obtain a calcium hypochlorite composition comprising 75.1% of calcium hypochlorite, 6.5% of calcium hydroxide, 9.5% of water content, 1.5% of calcium chloride and 5.5% of sodium chloride.

The composition thus obtained was subjected to tests which were conducted in the same manner as in Embodiment Example 1. The decomposition rate of calcium hypochlorite was 5.0% at 40° C. over the period of 50 days and 12.0% at 65° C. over the period of two days.

Further, an experiment was conducted for the purpose of comparison in the same manner as described in the foregoing with the exception of that: In this case, the calcium hydroxide powder was not added while only 10 parts of the sodium chloride powder of 99% purity was added. A calcium hypochlorite composition obtained in this manner comprised 74.4% of calcium hypochlorite, 1.2% of calcium hydroxide, 9.2% of water content, 1.5% of calcium chloride and 10.5% of sodium chloride.

The composition thus obtained was also subjected to the tests in the same manner as in Embodiment Example 1 of find that the decomposition rate of calcium hypochlorite was 23.0% at 40° C. over the period of 50 days and 27.0% at 65° C. over the period of two days.

What is claimed is:

1. A stable calcium hypochlorite composition having a calcium hypochlorite anhydride and/or a calcium hypochlorite dihydrate as main constituent thereof, said composition comprising at least 60 wt % of calcium hypochlorite, at least 5 wt % of calcium hydroxide, at least 4 wt % of water content and 5 wt % or less than that of calcium chloride.

2. A stable calcium hypochlorite composition according to claim 1 wherein said calcium hydroxide is virtually free calcium hydroxide.

3. A stable calcium hypochlorite composition according to claim 1 or 2 comprising 6–8 wt % of calcium hydroxide and 7–22 wt % of water content.

4. A method for manufacturing a stable calcium hypochlorite composition wherein calcium hydroxide is added to a raw calcium hypochlorite composition having a calcium hypochlorite anhydride and/or a calcium hypochlorite dihydrate as main constituent thereof to obtain a composition comprising at least 60 wt % of calcium hypochlorite, at least 5 wt % of calcium hydroxide, at least 4 wt % of water content and 5 wt % or less than of calcium chloride.

5. A method for preparing a stable calcium hypochlorite composition according to claim 4 wherein said raw calcium hypochlorite composition includes water content not exceeding 70 parts by weight and calcium chloride not exceeding 8 parts by weight of 100 of calcium hypochlorite.

6. A method for preparing a stable calcium hypochlorite composition according to claim 4 or 5 wherein said calcium hydroxide is at least 2 parts by weight as Ca(OH)$_2$ to 100 of said raw calcium hypochlorite composition.

7. A method for preparing a stable calcium hypochlorite composition according to claim 4 or 5 wherein said calcium hydroxide is between 5 and 10 parts by weight as Ca(OH)$_2$ to 100 parts of said raw calcium hypochlorite composition.

8. A method for preparing a stable calcium hypochlorite composition according to claim 4 or 5 wherein said calcium hydroxide to be added is a free calcium hydroxide powder.

9. A method for preparing a stable calcium hypochlorite composition according to claim 8 wherein said calcium hydroxide contains water in quantity not exceeding 10 wt % and calcium carbonate not exceeding 5 wt %, said calcium hydroxide being of particle size capable of passing through a 200 mesh screen.

10. A method for preparing a stable calcium hypochlorite composition according to claim 4 or 5 comprising 6–8 wt % of said calcium hydroxide and 7–22 wt % of water content.

11. A method for preparing a stable calcium hypochlorite composition according to claim 4 or 5 wherein said raw calcium hypochlorite composition contains as main constituent thereof a coarse calcium hypochlorite dihydrate or a dried product obtained therefrom, said coarse calcium hypochlorite dihydrate being obtained by adding as seed crystals, in crystallizing a calcium hypochlorite dihydrate, a prismatic calcium hypochlorite dihydrate having its ases a and b (in the direction of width) and axis c (in the direction of thickness) in the ratio of:

$$0.5 \leq b/a \leq 2.0$$
$$c/a \geq 1.5$$

and having the axis c measure at least 5 microns.

* * * * *